United States Patent [19]

Hashimoto et al.

[11] Patent Number: 4,906,618

[45] Date of Patent: Mar. 6, 1990

[54] PROPHYLACTIC AND THERAPEUTIC AGENT AGAINST SWINE DYSENTERY

[75] Inventors: Seiji Hashimoto, Umezono; Michio Yamashita, Namiki; Kazuyoshi Umehara, Matsushiro; Kiyohiko Kunugita, Shimohirooka; Masanobu Kohsaka, Sengen, all of Japan

[73] Assignee: Fujisawa Pharmaceutical Co., Ltd., Osaka, Japan

[21] Appl. No.: 16,741

[22] Filed: Feb. 19, 1987

[30] Foreign Application Priority Data

Mar. 4, 1986 [GB] United Kingdom ................. 8605245

[51] Int. Cl.$^4$ ............................................. A61K 31/70
[52] U.S. Cl. ..................................................... 514/25
[58] Field of Search ........................................... 514/25

[56] References Cited

U.S. PATENT DOCUMENTS 4,794,105 12/1988 Hasegawa et al. ................... 514/25

OTHER PUBLICATIONS

Wakisaka et al., The J of Antibiotics, vol. 33, Jul. 1980, No. 7, pp. 695–704.

Primary Examiner—Jerome D. Goldberg
Attorney, Agent, or Firm—Oblon, Spivak, McClelland, Maier & Neustadt

[57] ABSTRACT

This invention relates to a method for promoting the growth of growing animals with compounds selected from WS-1627A; WS-1627B; WS-1627C and WS-1627D or salts thereof.

3 Claims, 2 Drawing Sheets

FIG. 1

FIG. 2

PROPHYLACTIC AND THERAPEUTIC AGENT AGAINST SWINE DYSENTERY

This invention relates to an agent for preventing or treating swine dysentery and for promoting the growth of growing animals. More particularly, it relates to a prophylactic or therapeutic composition against swine dysentery which comprises, as effective ingredient(s), one or more compound(s) selected from WS-1627A, WS-1627B, WS-1627C and WS-1627D, or salts thereof, to a use of one or more compound(s) selected from WS-1627A, WS-1627B, WS-1627C and WS-1627D or salt thereof, for the manufacture of a veterinary medicine for preventing or treating swine dysentery, and to a method for preventing or treating swine dysentery by administering an effective amount of said compound(s) to swine suffering from or susceptible to swine dysentery.

Further, it relates to an animal growth promotant composition comprising the same ingredient(s) as mentioned above.

Heretofore, the breeding of swines has been developing in a large scale, swine dysentery has been prevalent and thereby a great deal of damage was done to the swine industry. On the other hand, it has been found from various investigations that the major causative microorganism of swine dysentery is *Treponema hyodysenteriae*.

Many chemotherapeutic agents and antibiotics have been evaluated for their prophylactic or therapeutic effectiveness against swine dysentery. However, these substances are not satisfactory in respects of their effects, side effects and/or toxicities. For example, the most broadly used synthetic antimicrobial agent for this purpose, carbadox is a strong mutagenic substance.

In the course of screening program for novel prophylactic or therapeutic agents from soil samples, the inventors of the present invention newly found out that four substances obtained from a cultured broth of a newly isolated microorganism, *Streptomyces noboritoensis* subsp. *amamiensis* subsp. nov. No. 1627, have strong antimicrobial activities against *Treponema hyodysenteriae*. Then, these substances were named WS-1627A, WS-1627B, WS-1627C and WS-1627D, respectively.

Further, the inventors of this invention also found out that these substances have an animal growth promoting effect.

The WS-1627A, WS-1627B, WS-1627C and WS-1627D have the following physicochemical properties.

Figure 1:
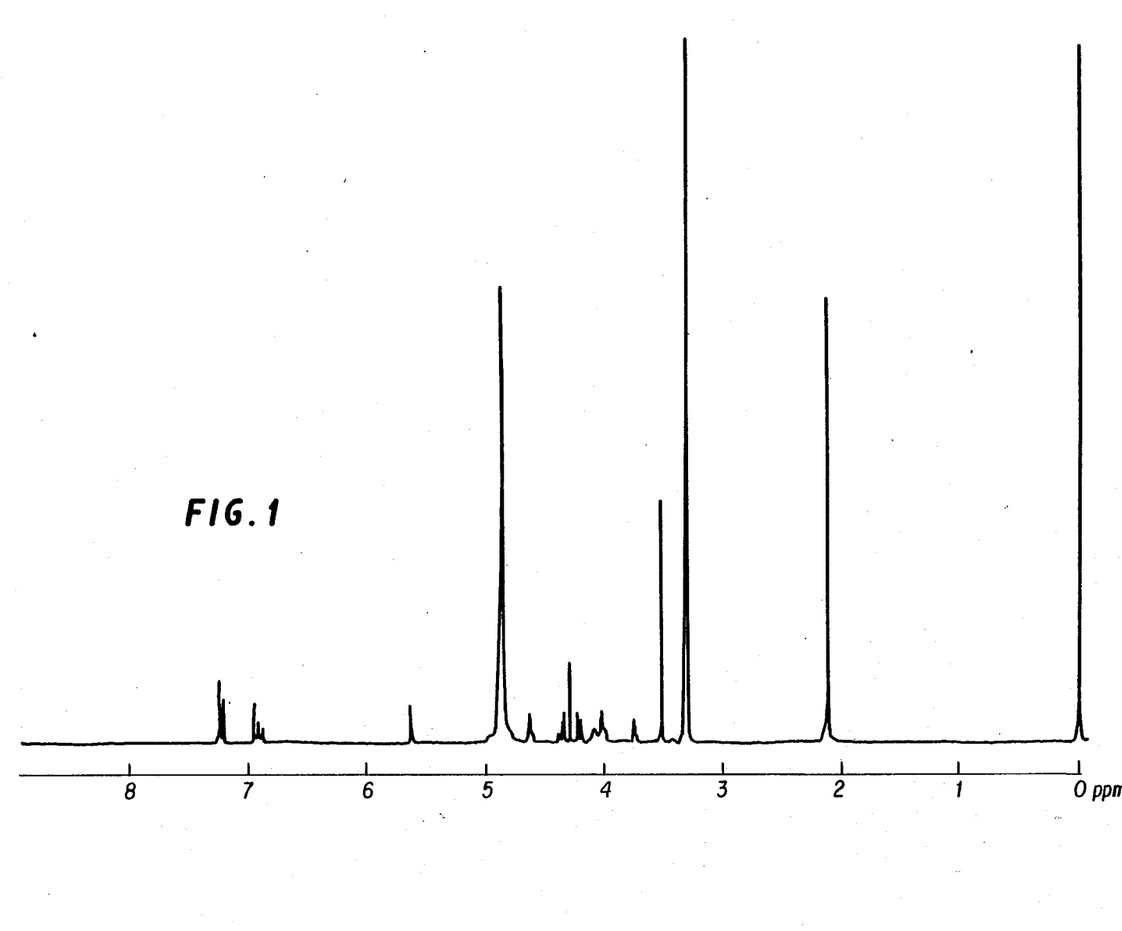

WS-1627A (a) Appearance: White powder.
(b) Melting point: 104–107° C.
(c) Optical rotation: $[\alpha]_D^{22} = -125.0°$ (C=1.0, H$_2$O).
(d) Molecular weight: 513 [SIMS:m/z 514 (M$^+$ +1)].
(e) Elemental analysis (%): C 53.71; H 6.07; N 2.91.
(f) UV absorption spectrum: $\lambda_{max}$ H$_2$O nm ($\epsilon$): 300 (sh, 22800), 270 (34800), 214 (46000). $\lambda_{max}$ 0.1NHCl nm ($\epsilon$): 300 (sh, 22500), 270 (34600), 214 (45900). $\lambda_{max}$ 0.1N NaOH nm ($\epsilon$): 323 (sh, 15350), 285 (sh, 25900), 249 (45400), 230 (sh, 41500).
(g) IR absorption spectrum: $\nu_{max}$ KBr: 3700–3000, 2930, 1720, 1700, 1640, 1610, 1510, 1420, 1360, 1320, 1270, 1250, 1200, 1130, 1100, 1060, 1025, 960, 900, 840, 800 cm$^{-1}$.
(h) $^1$H NMR absorption spectrum: (D$_2$O) (as shown in FIG. 1) $\delta$ ppm: 212 (6H, s), 3.51 (3H, s), 3.72–3.76 (1H, m), 3.99–4.15 (4H, m), 4.18–4.39 (3H, m), 4.62–4.65 (1H, m), 5.62 (1H, d, J=4.3 Hz), 6.86–6.95 (2H, m), 7.20–7.25 (2H, m).
(i) Solubility: Soluble: Water, methanol. Insoluble: Acetone, ethyl acetate, chloroform.
(j) Color reaction: Positive: Ferric chloride reaction, reaction with cerium sulfate and iodine vapor. Negative: Molish's reaction, Ninhydrin reaction.
(k) Property of substance: Acidic substance.

From the above physicochemical properties and other investigations, it can be judged that the WS-1627A is a known antibiotic, KA-3093 [Cf. Japan Kokai No. 99495/1981].

WS-1627B (a) Appearance: White powder.
(b) Melting point: 107–110° C.
(c) Optical rotation: $[\alpha]_D^{20} = -126.5°$ (C=1.0, H$_2$O).
(d) Molecular weight: 511 [SIMS: m/z 512 (M$^+$ +1)].
(e) Elemental analysis (%): C 53.83; H 5.86; N 2.63.
(f) UV absorption spectrum: $\lambda_{max}$ H$_2$O nm ($\epsilon$): 300 (sh, 22700), 270 (34700), 214 (46000). $\lambda_{max}$ 0.1NHCl nm ($\epsilon$): 300 (sh, 22500), 270 (34500), 214 (45800). $\lambda_{max}$ 0.1NaOH nm ($\epsilon$): 323 (15300), 285 (sh, 25800), 249 (45200), 232 (sh, 41400).
(g) IR absorption spectrum: $\nu_{max}$ KBr: 3700–3000, 2920, 1720, 1700, 1640, 1610, 1510, 1430, 1360, 1320, 1270, 1250, 1210, 1160, 1130, 1100, 1060, 1000, 960, 920, 840, 810 cm$^{-1}$.
(h) $^1$H NMR absorption spectrum: D$_2$O) $\delta$ ppm: 2.12 (6H, s), 3.80–3.84 (1H, m), 3.95–4.00 (1H, m) 4.17–4.40 (6H, m), 4.49–4.53 (1H, m), 4.80 (1H, s), 5.23 (1H, s), 5.62 (1H, d, J=4.3 Hz), 6.87–6.95 (2H, m), 7.20–7.26 (2H, m).
(i) Solubility: Soluble: Water, methanol. Insoluble: Acetone, ethyl acetate, chloroform.
(j) Color reaction: Positive: Ferric chloride reaction, reaction with cerium sulfate and iodine vapor. Negative: Molish's reaction, Ninhydrin reaction.
(k) Property of substance: Acidic substance.

From the above physicochemical properties and other investigations, it can be judged that the WS-1627B is a known antibiotic, hygromycin [cf. THE MERCK INDEX TENTH EDITION Page 708 (1983)].

Figure 2:
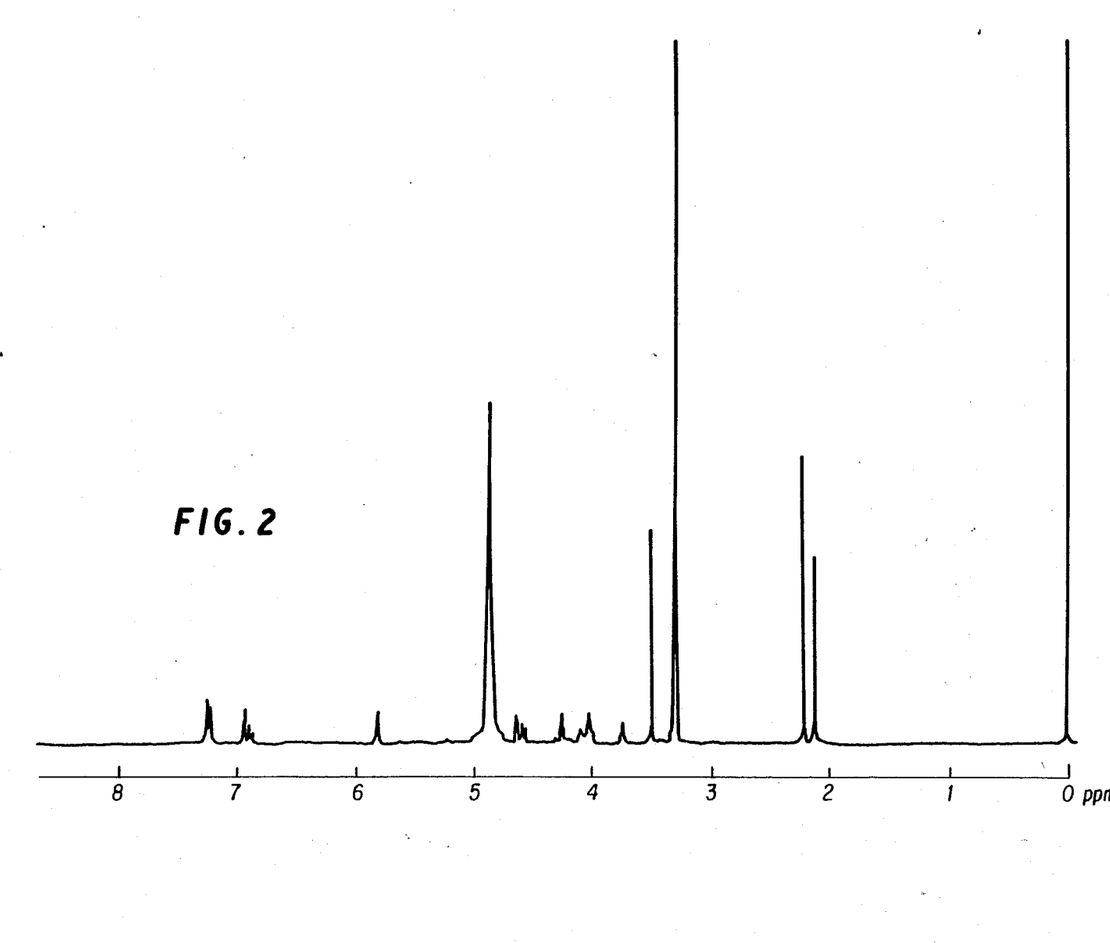

WS-1627C (a) Appearance: White powder.
(b) Melting point: 110–113° C.
(c) Optical rotation: $[\alpha]_D^{20} = -62.0°$ (C=1.0, H$_2$O).
(d) Molecular weight: 513 [SIMS: m/z 514 (M$^+$ +1)].
(e) Elemental analysis (%): C 53.65; H 6.33; N 2.95.
(f) UV absorption spectrum: $\lambda_{max}$ H$_2$O nm ($\epsilon$): 300 (sh, 22,750), 270 (34,750), 214 (46,000). $\lambda_{max}$ 0.1NHCl nm ($\epsilon$): 300 (sh, 22,500), 270 (34,750), 214 (46,000). $\lambda_{max}$ 0.1N NaOH nm ($\epsilon$): 323 (15,350), 285 (sh, 25,800), 249 (45,200), 232 (sh, 41,400).
(g) IR absorption spectrum: $\nu_{max}$ KBr: 3700–3000, 2900, 2700, 1720, 1700, 1640, 1600, 1510, 1420, 1350, 1330, 1260, 1250, 1200, 1120, 1100, 1050, 1020, 960, 900, 830, 800 cm$^{-1}$.
(h) $^1$H NMR absorption spectrum: (CD$_3$OD) (as shown in FIG. 2) $\delta$ ppm: 2.12 (3H, s), 2.21 (3H, s), 3.51 (3H, s), 3.73–3.75 (1H, m), 4.00–4.14 (4H, m), 4.20–4.30 (2H, m), 4.55–4.65 (2H, m), 5.83 (1H, d, J=4 Hz), 6.85–6.94 (2H, m), 7.21–7.25 (2H, m).
(i) Solubility: Soluble: Water, methanol. Insoluble: Acetone, ethyl acetate, chloroform.

(j) Color reaction: Positive: Ferric chloride reaction, reaction with cerium sulfate and iodine vapor. Negative: Molish's reaction, Ninhydrin reaction.

(k) Property of substance: Acidic substance.

From the above physicochemical properties and other investigations, it can be judged that the WS-1627C is a new epimer of KA-3093.

WS-1627D (a) Appearance: White powder.

(b) Melting point: 114°–117° C.

(c) Optical rotation: $[\alpha]_D^{20} = -93.1°$ (C=1.0, H$_2$O).

(d) Molecular weight: 511 [m/z 512 (M$^+$+1)].

(e) Elemental analysis (%): C 53.91; H 5.82; N 2.80.

(f) UV absorption spectrum: $\lambda_{max}$ H$_2$O nm ($\epsilon$): 300 (sh, 22,700), 270 (34,700), 214 (46,000). $\lambda_{max}$ 0.1NHCl nm ($\epsilon$): 300 (sh, 22,500), 270 (34,600), 214 (45,900). $\lambda_{max}$ 0.1N NaOH nm ($\epsilon$): 323 (sh, 15,300), 285 (sh, 25,900), 249 (45,400), 232 (41,400).

(g) IR absorption spectrum: $\nu_{max}^{KBr}$: 3700–3000, 2900, 1720, 1710, 1640, 1620, 1600, 1510, 1430, 1350, 1270, 1250, 1210, 1130, 1100, 1050, 1020, 960, 920, 900, 880, 840, 810 cm$^{-1}$.

(h) $^1$H NMR absorption spectrum: (CD$_3$OD) δ ppm: 2.12 (3H, m), 2.21 (3H, s), 3.80–3.82 (1H, m), 3.94–4.00 (1H, m), 4.16–4.29 (4H, m), 4.49–4.59 (2H, m), 4.79 (1H, s), 5.23 (1H, s), 5.82 (1H, d, J=4 Hz), 6.85–6.89 (2H, m), 7.20–7.25 (2H, m).

(i) Solubility: Soluble: Water, methanol. Insoluble: Acetone, ethyl acetate, chloroform.

(j) Color reaction: Positive: Ferric chloride reaction, reaction with cerium sulfate and iodine vapor. Negative: Molish's reaction, Ninhydrin reaction.

(k) Properties of substance: Acidic substance.

From the above physicochemical properties and other investigations, it can be judged that WS-1627D is a known antibiotic, epi-hygromycin [cf. THE JOURNAL OF ANTIBIOTICS VOL. XXXIII Pages 695 (1980)].

From the above data, chemical structures of WS-1627A, WS-1627B, WS-1627C and WS-1627D can be represented as follows.

$R_1$ = COCH$_3$  WS-1627A
$R_2$ = H  (KA-3093)

$R_1$ = H
$R_2$ = COCH$_3$  WS-1627C $R_1$ = COCH$_3$  WS-1627B
$R_2$ = H  (Hygromycin)

$R_1$ = H
$R_2$ = COCH$_3$  WS-1627D (epi-Hygromycin)

The WS-1627A, WS-1627B, WS-1627C and WS-1627D can be prepared by culturing a WS-1627A, WS-1627B, WS-1627C and/or WS-1627D-producing strain belonging to the genus Streptomyces in a nutrient medium and recovering the WS-1627A, WS-1627B, WS-1627C and WS-1627D from the cultured broth.

Among a WS-1627A, WS-1627B, WS-1627C and/or WS-1627D-producing strain belonging to the genus Streptomyces, *Streptomyces noboritoensis* subsp. *amamiensis* No. 1627 was newly isolated from a soil sample collected at Amami-Oshima, Japan.

Lyophilized samples of the newly isolated *Streptomyces noboritoensis* subsp. *amamiensis* No. 1627 have been deposited with an International Depositary Authority on Budapest Treaty, Fermentation Research Institute, Agency of Industrial Science and Technology residing at Yatabe-cho higashi No. 1-1-3, Tsukuba-gun, Ibaraki-ken, Japan, under the number FERM BP-1275(formerly, FERM P-8069) since January 25, 1985.

Further, *Streptomyces hygroscopicus* IFO 13472 can also produce the WS-1627A, WS-1627B, WS-1627C and WS-1627D in the cultured broth thereof.

It is to be understood that the production of the WS-1627A, WS-1627B, WS-1627C and WS-1627D is not limited to the use of the particular organisms described herein, which are given for illustrative purpose only. This invention also includes the use of any mutants which can be produced from the described organisms by conventional means, such as X-rays, ultra-violet radiation, treatment with N-methyl-N'-nitro-N-nitrosoguanidine, 2-aminopurine and the like.

*Streptomyces noboritoensis* subsp. *amamiensis* No. 1627 has the following morphological, cultural and physiological characteristics.

Morphological observations were made with light and electron microscopes from cultures grown at 30° C. for 14 days on yeast-malt extract agar, oatmeal agar and inorganic salts-starch agar. The mature sporophores were formed Rectiflexibiles with more than 30 spores in each chain. Aerial mycelium was poorly developed on some of examined media. The spore surfaces were smooth.

Cultural characteristics were observed on ten kinds of media described by Shirling and Gottlieb [Vide. International Journal of Systematic Bacteriology 16, 313–340 (1966)] and by Waksman [Vide. S. A. Waksman "The Actinomycetes Vol. 2 (1961)]. The incubation was made at 30° C. for 14 days. The color names used in this study were based on Color Standard (Nihon Shikisai Co., Ltd.). Colonies belonged to the gray or red color series when grown on yeast-malt extract agar and inorganic salt-starch agar. Melanoid pigment was produced on tyrosine agar, but not on peptone-yeast extract-iron agar. Soluble pigment was produced in some of examined media. The results are shown in the following Table 1 in comparison with characteristics of *Streptomyces noboritoensis* IFO 13065.

TABLE 1

Cultural characteristics of the strain No. 1627 and *Streptomyces noboritoensis* IFO 13065

| Medium | | No. 1627 | IFO 13065 |
|---|---|---|---|
| Oatmeal agar | G | Poor to moderate | Poor |
| | A | None | None |
| | R | Dark yellowish brown | Dark yellowish brown |
| | S | Pale yellowish brown | Pale yellow orange |
| Yeast-malt extract agar | G | Moderate | Moderate |
| | A | Light gray | Gray |
| | R | Dark brown | Reddish brown |
| | S | Brown | Brown |
| Inorganic salts-starch agar | G | Moderate | Moderate |
| | A | Pale pinkish white cottony | Pale yellow orange, powdery |
| | R | Reddish brown | Reddish brown to black |
| | S | None | None |
| Glucose-asparagine agar | G | Moderate | Moderate |
| | A | Grayish white, cottony | Grayish white, powdery |
| | R | Light brown | Brown |
| | S | Pale yellow orange | Pale yellow orange |
| Glycerin-asparagine agar | G | Moderate | Moderate |
| | A | Light gray | Light gray |
| | R | Reddish brown | Dull reddish brown |
| | S | Pale brown | Brown |
| Czapek agar | G | Poor | Poor |
| | A | None | White |
| | R | Colorless | Colorless |
| | S | None | None |
| Nutrient agar | G | Poor | Poor |
| | A | None | None |
| | R | Colorless | Colorless |
| | S | None | None |
| Potato-dextrose agar | G | Moderate | Moderate |
| | A | Gray, poor | None |
| | R | Grayish black | Dull red |
| | S | Brown | None |
| Tyrosine agar | G | Moderate | Moderate |
| | A | Gray, poor | Light gray, poor |
| | R | Dark gray to dark brown | Dark brown |
| | S | Brown | Brown |
| Peptone-yeast extract-iron agar | G | Moderate | Moderate |
| | A | None | None |
| | R | Colorless | Colorless |
| | S | None | Brown |

Abbreviation:
G = growth,
A = aerial mycelium,
R = reverse side color,
S = soluble pigment Cell wall analysis was performed by the methods of Becker et al [Vide. Applied Microbiology 12, 421–423 (1964)] and Yamaguchi [Vide. Journal of Bacteriology 89, 444–453 (1965)]. Analysis of whole cell hydrolysates showed the presence of LL-diaminopimelic acid. Accordingly, the cell wall of this strain is believed to be of type I.

Physiological properties of the strain No. 1627 were determined according to Shirling and Gottlieb [Vide. The same literature as mentioned above]. Temperature range for growth was from 12° C. to 36° C. with optimum temperature from 26° C. to 28° C. Starch hydrolysis, melanin production and gelatin liquefaction were positive. The results are summarized in Table 2 in comparison with characteristics of *Streptomyces noboritoensis* IFO 13065.

TABLE 2

Physiological properties of the strain No. 1627 and *Streptomyces noboritoensis* IFO 13065.

| | No. 1627 | IFO 13065 |
|---|---|---|
| Temperature range for growth | 12° C.–36° C. | 8° C.–38° C. |
| Optimum temperature | 26° C.–28° C. | 24° C.–28° C. |
| Nitrate reduction | Negative | Negative |
| Starch hydrolysis | Positive | Positive |
| Milk coagulation | Negative | Negative |
| Milk peptonization | Negative | Positive |
| Melanin production | Positive | Positive |
| Gelatin liquefaction | Positive | Positive |
| H$_2$S production | Negative | Positive |
| NaCl tolerance | 7%<-<10% | 7%<-<10% |

Utilization of carbon sources was examined according to the method of Pridham and Gottlieb [Vide. Journal of Bacteriology 56, 107–114 (1948)]. The growth was observed after 14 days incubation at 30° C. Carbon sources utilization of this strain is shown in Table 3 in comparison with those of *Streptomyces noboritoensis* IFO 13065.

TABLE 3

Carbon sources utilization of strain No. 1627 and *Streptomyces noboritoensis* IFO 13065.

| Carbon source | No. 1627 | IFO 13065 |
|---|---|---|
| D-Glucose | + | + |
| Sucrose | + | + |
| Glycerin | + | + |
| D-Xylose | + | + |
| D-fructose | − | + |
| Lactose | + | + |
| Maltose | + | + |
| Rhamnose | − | − |
| Raffinose | + | + |
| D-Galactose | + | + |
| L-Arabinose | + | + |
| D-Mannose | + | + |
| D-Trehalose | + | + |
| Inositol | + | − |
| Mannitol | − | + |
| Inulin | − | − |
| Cellulose | − | − |
| Salicin | − | + |
| Chitin | − | − |
| Sodium citrate | + | + |
| Sodium succinate | + | + |
| Sodium acetate | ± | − |

Symbols:
+ = utilization,
± = doubtful utilization,
− = no utilization

Microscopic studies and cell wall composition analysis indicate that the strain No. 1627 belongs to the genus Streptomyces Waksman and Henrici 1943. Accordingly, a comparison of this strain was made with various Streptomyces species in the light of the published descriptions [Vide. International Journal of Systematic Bacteriology 18, 69–189, 279–392 (1968) and 19, 391–512 (1969), and Bergey's Manual of Determinative Bacteriology 8th Edition (1974)].

As the results of the comparison, the strain No. 1627 was considered to resemble *Streptomyces noboritoensis* Isono et al. 1957. Therefore, the strain No. 1627 was compared with the corresponding *S. noboritoensis* IFO 13065.

As the results of comparison, cultural characteristics of the strain No. 1627 are different from those of *S. noboritoensis* on inorganic salts-starch agar, potato-dextose agar and peptone-yeast extract-iron agar. Milk peptonization and H₂S production of the strain No. 1627 are negative, but those of *S. noboritoensis* are positive. In carbon utilization, the strain No. 1627 can utilize inositol, but *S. noboritoensis* can not utilize it. And, the strain No. 1627 can not utilize D-fructose, mannitol and salicin, but *S. noboritoensis* can utilize them. As the results of comparison as mentioned above, there are some differences between the strain No. 1627 and *S. noboritoensis*. However, morphological and cultural characteristics were similar each other on numerous media. Therefore, the strain No. 1627 can be considered to belong to *S. noboritoensis*. Considering several differences of the strain No. 1627 from *S. noboritoensis*, it is reasonable that the strain No. 1627 is regarded as new subspecies of *S. noboritoensis*. Therefore, the strain No. 1627 has been designated as *Streptomyces noboritoensis* subsp. *amamiensis* No. 1627.

The WS-1627A, B, C and D can be produced by culturing a WS-1627 A, B, C and/or D producing strain belonging to the genus Streptomyces in a nutrient medium.

In general, the WS-1627A, B, C and D can be produced by culturing the WS-1627A, B, C and/or D producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nitrients, are also suitable for use. When desired, there may be added to medium such as mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the WS-1627A, B, C and D.

For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the object compounds. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the object compounds.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced WS-1627A, B, C and D can be recovered from the culture medium by conventional means which are commonly used for the recovery of other fermentation products such as antibiotics.

In general, most of the WS-1627A, B, C and D produced are found in the culture filtrate, and accordingly the object compounds can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The WS-1627A, B, C and D can be separated each other and isolated, for example, by subjecting a crude material comprising WS-1627A, B, C and D to a low pressure and high performance liquid chromatography using reverse phase silica gel [e.g. Lichroprep RP-8, RP-18 (trademark, made by E. Merk), μBondapak C₁₈ (trademark, made by Waters Associates)].

The WS-1627A, B, C and D as obtained in their free forms may be converted to a salt with inorganic or organic base such as sodium salt, potassium salt, triethylamine salt and the like. The WS-1627A, B, C and D or their salts can orally or parenterally be administered as a prophylactic and therapeutic agent against swine dysentery to swine and as a growth promoting agent to growing animals (e.g. piglet, chick, etc.) in a conventional manner. In cases that the WS-1627A, B, C and D and their salts are orally administered to animals one or more effective ingredient(s) selected from the WS-1627A, B, C, D and their salts may usually be administered as it is or in admixture with a suitable carrier (e.g. water, kaolin, talc, calcium carbonate, lactose, etc.) or in admixture with a feed. More particularly, the effective ingredient(s) may be administered to animals as a drinking water in the form of aqueous solution; or as a tablet, granule or capsule in the form of preparations which comprises the effective ingredient(s) and suitable non-toxic carrier(s) as exemplified above; or as a ration in the form of the composition which comprises the effective ingredient(s) and animal feed.

Further, in cases that the WS-1627A, B, C or D or mixture thereof is parenterally administered to animals, a conventional and suitable injection preparations which comprises the effective ingredient(s) and suitable non-toxic carrier(s) (e.g. water, etc.) can be employed.

In connection of the form of administering the feed composition as mentioned above, the ration comprising one or more effective ingredient(s) selected from the WS-1627A, B, C and D and their salts can be prepared in a conventional manner, namely by admixing the effective ingredient(s) with basal ration.

The dosage of the effective ingredient(s) to animals may be varied over a very wide range depending upon various factors such as kind of animals, growth period, administration route and the like. In general, for the purpose of the treatment of swine dysentery, preferred dosage of the effective ingredients to swine may be selected from the range within 0.1-100 mg/kg/day. Levels of the effective ingredient(s) in the feed and drinking water which are construed as preferably and anticipated to treat the swine dysentery and to promote growth of growing animals may be in an amount between about 1 and about 500 ppm, and 0.5-250 ppm, respectively.

For the purpose of the prophylaxis of swine dysentery, preferred dosage of the effective ingredients to swine may be selected from the range within 0.02-25 mg/kg/day.

Further, in the acute toxicity test, each of five ddy mice (5-week old, male, 20 g in weight), was intraveneously given a single dose of WS-1627A, B, C or D 20 mg (1g/kg) and all survived. During 10 days of observation after injection, no toxic symptom was observed.

The following Tests and Examples are given to illustrate this invention, but it should be understood that they are not intended to limit this invention.

TEST 1.

(In vitro activity of WS-1627A, B, C and D against *Treponema hyodysenteriae*)

The test organisms were grown anaerobically for 96 hours on Trypticase soy agar plate supplemented with 5% sheep blood. Appropriate amounts of physiological saline solution were poured into each agar plate to make a cell-suspension of test organism, which was finally adjusted at the cell density of $10^6$ colony forming units (CFU)/ml. Freshly prepared Trypticase soy agar plates supplemented with 5% sheep blood which were containing serial two-fold dilutions of each of the compounds as mentioned below were inoculated with a loopful (about 5 μl) of the above-mentioned cell-suspension. The MIC (minimum inhibitory concentration) values were determined after 72 hours of anaerobical incubation at 37° C. in Gas Pak jars.

The results are shown in the following table.

TABLE 3

| Stains of Treponema hyodysenteriae | MIC (μg/ml) | | | |
|---|---|---|---|---|
| | WS1627A | WS1627B | WS1627C | WS1627D |
| ATCC 31212 | 3.2 | <0.8 | 6.3 | <0.8 |
| DJ70 | 1.6 | <0.8 | 3.2 | <0.8 |
| TH81013 | 6.4 | <0.8 | 12.8 | <0.8 |
| S5709 | <0.8 | <0.8 | 1.6 | <0.8 |

TEST 2.

(Protective effect of the WS-1627A, B, C and D against experimental infection of *Treponema hyodysenteriae* in mice)

5 week-old mice (ddy, ♂) were used in these experiments. Mice were orally infected with $1.8 \times 10^7$ cells of *Treponema hyodysenteriae* S5709 grown for 96 hours on Trypticase soy agar plate supplemented with 5% sheep blood. On the first and second day after challenge, test compounds were given by oral administration once a day. One week after infection, the efficacy of the antibiotics on mice suffering from dysentery was determined as follows. Cecum contents from infected mice were suspended in 2 ml of saline solution, diluted twenty times with Trypticase soy medium supplemented with 5% sheep blood and cultured for T. hyodysenteriae on agar plate of Trypticase soy medium supplemented with 5% sheep blood at 37° C. for 72 hours in Gas Pak jars. The numbers of *T. hyodysenteriae* colony appeared on the plates were counted. Mice that gave no colony formations of *T. hyodysenteriae* were regarded as cured mice.

The results are shown in the following table.

TABLE 4

| Test compound and Dosage | cured/treated |
|---|---|
| Vehicle (water) | 0/7 |
| WS1627A 5 mg/kg | 4/7 |
| WS1627B 5 mg/kg | 7/7 |
| WS1627C 5 mg/kg | 4/7 |
| WS1627D 5 mg/kg | 4/7 |

EXAMPLE 1

Preparation of WS-1627 A and C

An aqueous seed medium (80 ml) containing 1% corn starch, 1% glycerin, 0.5% glucose, 1% cotton seed meal, 0.5% dried yeast, 0.5% corn steep liquor, 0.2% calcium carbonate (pH 6.5) into each of ten 250 ml Erlenmeyer flasks and sterilized at 120° C. for 30 minutes. A loopful of *Streptomyces noboritoensis* subsp. *amamiensis* No. 1627 on matured slant culture was inoculated to the seed medium. The flasks were shaken on a rotary shaker at 30° C. for 3 days.

An aqueous production medium (18 l) containing 3% starch, 2% sucrose, 0.5% cotton seed meal, 0.5% dried yeast, 0.5% gluten meal, 0.05% magnesium sulfate heptahydrate, 0.05% sodium chloride, 0.0004% cobaltous chloride hexahydrate, 0.00005% sodium iodide, 0.2% calcium carbonate (pH 6.8) was poured into each of two 30 l stainless steel fermenters and sterilized at 120° C. for 30 minutes. The resultant seed culture broth (360 ml) was inoculated to each of the production medium and cultured at 30° C. for 3 days, agitated at 300 rpm and aerated at 20 liters per minute.

The cultured broth (35 l) was filtrated with the aid of diatomaceous earth (500 g). The filtrate (32 l, pH 7.2) was passed through a column of activated charcoal (3.2 l). The column was washed with water (7 l) and eluted with 60% aqueous acetone (15 l). The eluate was concentrated to a volume of 1 liter under reduced pressure. The concentrate was chromatographed on CM-Sephadex C-25 (H+, made by Pharmacia Fine Chemicals A B) column (2 l). The column was developed with water. The active fraction (4 l) was concentrated under reduced pressure. The residue was chromatographed on a column (200 ml) of silica gel using saturated aqueous n-butanol as developing solvent. The active fraction (320 ml) was combined and concentrated to a volume of 50 ml under reduced pressure. The resultant solution was chromatographed on a column (50 ml) of nonionic adsorption resin, HP-20 (trademark, made by Mitsubishi Chemical Industries Ltd.) to remove the silica gel. The column was washed with water (200 ml) and 20% aqueous methanol (200 ml) and then eluted with 40% aqueous methanol (250 ml). The eluate was concentrated under reduced pressure and the resultant solution was freeze-dried to give a pale yellow powder (900 mg).

The crude powder was dissolved in 30% aqueous methanol (9 ml) and applied to a column of low pressure liquid chromatography using reverse phase silica gel [Lichroprep RP-8 (trademark) made by E. Merck, size B: 310×25 mm, 40–63 μm, detected by UV absorbance at 254 nm, flow rate 10 ml/min] with 30% aqueous methanol. The first fractions (from 220 ml to 290 ml) were collected and concentrated under reduced pressure. The resultant solution was freeze-dried to give a white powder (Powder I, 150 mg) containing WS-1627A and WS-1627C. The continuous fractions (from 310 ml to 360 ml) were collected and concentrated under reduced pressure. The resultant solution was freeze-dried to give a white powder (Powder II, 12.7 mg) containing WS-1627B and WS-1627D. The powder I (140 mg) was further purified, in seven separate runs, using a high performance liquid chromatography. Each portion (20 mg) of the starting charge was dissolved in 20% aqueous methanol (0.2 ml) and applied to a column of reverse phase silica gel (μBondapak $C_{18}$ (trademark) made by Waters Associates, 7.8×30 mm, 8–10 μm, detected by UV absorbance at 254 nm, flow rate 2.5 ml/min) with 20% aqueous methanol. The first fractions (from 45 ml to 50 ml) of each of the seven chromatographic separation were combined and concentrated under reduced pressure. The resultant solution was freeze-dried to give a white powder (15.8 mg) of WS-1627C. The continuous fractions (from 52 ml to 60 ml) of each of the seven chromatographic separations were combined and concentrated under reduced pressure. The resultant solution was freeze-dried to give a white powder (117 mg) of WS-1627A.

EXAMPLE 2

Preparation of WS-1627B and D

An aqueous seed medium (160 ml) containing 1% corn starch, 1% glycerin, 0.5% glucose, 1% cotton seed meal, 0.5% dried yeast, 0.5% corn steep liquor, 0.2% calcium carbonate (pH 6.5) into each of twenty three 500 ml Erlenmeyer flasks and sterilized at 120° C. for 30 minutes. A loopful of *Streptomyces noboritoensis* subsp. *amamiensis* No. 1627 on matured slant culture was inoculated to the seed medium. The flasks were shaken on a rotary shaker at 30° C. for 3 days. An aqueous production medium (180 l) containing 3% starch, 2% glycerin, 0.5% soy bean meal, 2% gluten meal, 0.05% magnesium sulfate heptahydrate, 0.05% sodium chloride, 0.0004% cobaltous chloride hexahydrate, 0.00005% sodium iodide, 0.2% calcium carbonate (pH 6.8) was poured into a 200 l stainless steel fermenter and sterilized at 120° C. for minutes. The resultant seed culture broth (3.6 l) was inoculated to the production medium and cultured at 30° C. for 4 days, agitated at 250 rpm and aerated at 20 liters per minute.

The culture broth (180 l) was filtrated with the aid of diatomaceous earth (2.5 kg). The filtrate (170 l, pH 7.2) was passed through a column (15 l) of activated charcoal. The column was washed with water (60 l) and 20% aqueous acetone (60 l) and then eluted with 60% aqueous acetone (75 l). The eluate was concentrated to a volume of 17 liters under reduced pressure. The concentrate was chromatographed on a column (4 l) of CM-Sephadex C-25 (H+). The column was developed with water. The activated fractions (3 l) was combined and concentrated under reduced pressure. The residue was chromatographed on a column (200 ml) of silica gel using saturated aqueous n-butanol as developing solvent. The active fractions were combined and concentrated to a volume of 100 ml under reduced pressure. The resultant solution was chromatographed on a column of HP-20 (200 ml) to remove the silica gel. The column was washed with water (800 ml) and 20% aqueous methanol (1200 ml) and then eluted with 40% aqueous methanol (1200 ml). The eluate was freeze-dried to give a pale yellow powder (3.62 g).

The crude powder was dissolved in 30% aqueous methanol (36 ml) and applied to a column of low pressure liquid chromatography using reverse phase silica gel [Lichroprep RP-8 (trademark) made by E. Merck, size B: 310×25 mm, 40–63 μm, detected by UV absorbance at 254 nm, flow rate 10 ml/min] with 30% aqueous methanol, in four separate runs. The first fractions (from 250 ml to 275 ml) of each of the four chromatographic separations were combined and concentrated under reduced pressure. The resultant solution was freeze-dried to give a white powder (Powder I, 108 mg) containing WS-1627A and WS-1627C. The continuous fractions (from 285 ml to 370 ml) of each of the four chromatographic separations were combined and concentrated under reduced pressure. The resultant solution was freeze-dried to give a white powder (Powder II, 2.07 g) containing WS-1627B and WS-1627D. The powder II (500 mg) was further purificated, in twenty five separated runs, using a high performance liquid chromatography. Each portion (20 mg) of the starting charge was dissolved in 20% aqueous methanol (0.2 ml) and applied to a column of reverse phase silica gel (μBondapak $C_{18}$ (trademark) made by Waters Associates, 7.8×30 mm, 8×10 μm, detected by UV absorbance at 254 nm, flow rate 2.5 ml/min) with 20% aqueous methanol. The first fractions (from 83 ml to 88 ml) of each of the twenty five chromatographic separations were combined and concentrated under reduced pressure. The resultant solution was freeze-dried to give a white powder (350 mg) of WS-1627D. The continuous fractions (from 93 ml to 100 ml) of each of twenty five chromatographic separations were combined and concentrated under reduced pressure. The resultant solution was freeze-dried to give a white powder (407 mg) of WS-1627B.

EXAMPLE 3

Preparation of WS-1627A, B, C and D

The WS-1627A, B, C and D were prepared in substantially the same manner as those of Example 1 and 2 except using *Streptomyces hygroscopicus* IFO 13472 in place of *Streptomyces noboritoensis* subsp. *amamiensis* No. 1627.

EXAMPLE 4

Therapeutic effect on experimentally induced swine dysentery

Seven piglets, LW (Landace×Large White crossbred) male, were used. The initial body weight at the time of inoculation of infective materials ranged from 6.5 to 8.5 kg. Piglets were divided into 4 groups (2 groups of 2 heads and 1 group of 1 head) and were maintained in stainless cages (90×90 cm) with raised plastic net floors at 28±2° C. Feed [Milk replacer for piglet] and water were supplied ad libitum except the duration of fasting. Infective materials used were prepared as follows. A total of 300 g of mucous haemorrhagic feces, large intestinal (from caecum through rectum) contents, and mucosa obtained from a clinically affected pig (3 days after onset of swine dysentery), which was previously inoculated into its caecum with pure culture of *Treponema hyodysenteriae* ATCC31212 (about $3 \times 10^9$ colony forming units/head) by surgical operation, were suspended, diluted finally 2.5 times with phosphate-bufferized saline and minced by biotron homogenizer (trademark, made by Biotrona Co., Ltd.).

For the purpose of infection, all piglets were inoculated individually with about 90 g of the infective materials after 22 hours' fasting.

All of those showed the clinical sign (watery and/or mucous haemorrhagic diarrhea) within 4 days after inoculation.

Treatment were done once a day for 2 consecutive days from the 5th day post inoculation.

The results are shown in the following Table.

TABLE 5

| Veterinary medicine | No. of pig | (average) days of recovery to normal stool | (average) days of disappearance** of fecal T. h*** |
|---|---|---|---|
| Vehicle* (Sterile water, orally 1 ml/kg body weight × 2 day) | 2 | >5 | >5 |
| WS1627 B (Solution in water, orally 2.5 mg/kg body weight × 2 day) | 2 | 2 | 2 |
| WS1627 B (Solution in water, intramuscularly 10 mg/kg body weight × 2 day) | 1 | 1 | 1 |

*Vehicle treatment means an infected, non-medicated group.
**Disappearance means the fecal treponemal number less than detection limit ($10^2$ colony-forming units/g of feces).
***T. h is the abbreviation of *Treponema hyodysenteriae*.

EXAMPLE 5

Growth promoting effect

Five sets of 24 pigs (33 days-old, LWD strain) were used. Each 24 pigs were divided into 4 groups, i.e. 3 treatment groups and a control group. Each group consisted of 3 barrows and 3 female pigs. They were fed continuously with the feed described in Table 6. Their body weight and feed consumption were observed for 6 weeks. The results are shown in Table 7.

TABLE 6-(a)

| Basal ration I | |
|---|---|
| Ingredient | % |
| Yellow maize | 63 |
| Wheat flour | 8 |
| Defatted Soybean meal | 16 |
| Skim milk | 5 |
| Fish meal | 3 |
| Vegetable oil | 1.5 |
| Tricalcium phosphate | 0.8 |
| Calcium carbonate | 1.2 |
| Sodium chloride | 0.4 |
| Zeolite | 1 |
| Nutritious premix* | 0.1 |

*Note:
The premix is composed of Vitamin A, $D_3$, E, $B_1$, $B_2$, $B_6$, $B_{12}$, nicotinic acid, Pantothenic acid, biotin, choline, lysine, methionine, zinc carbonate, calcium iodate, cobalt sulfate, ferric sulfate, cupric sulfate, manganese sulfate, ferrous fumarate, ethoxiquin and saccharin TABLE 6-(b)

| Feed composition fed to animals | |
|---|---|
| Feed Composition fed to Control group | The above basal ration I |
| Feed Composition fed to Treatment group I | The above basal ration I + WS-1627B 10 ppm |
| Feed Composition fed to Treatment group II | The above basal ration I + WS-1627B 20 ppm |
| Feed Composition fed to Treatment group III | The above basal ration I + WS-1627B 40 ppm |

TABLE 7

| | Control group | Treatment group | | |
|---|---|---|---|---|
| | | I | II | III |
| Average initial body weight (kg) | 10.0 | 10.0 | 10.0 | 10.0 |
| Average final body weight (kg) at the 6th week after the starting of the feeding | 28.0 | 29.6 | 29.2 | 28.9 |
| Average body weight gain (kg) at the 6th week after the feeding | 18.0 | 19.6 | 19.2 | 18.9 |
| Efficiency of feed utilization* | 2.19 | 2.05 | 2.11 | 2.09 |

*Note:

$$\text{Efficiency of feed utilization} = \frac{\text{Feed composition (kg) utilized for 6 weeks}}{\text{Average body weight gain (kg)}}$$

EXAMPLE 6

Growth promoting effect

8-Days-old male broiler chickens (chunky) were divided into 3 groups i.e. 2 treatment groups and a control group, each group of which consisted of 10 chicks. They were fed continuously with the feed described in Table 8. Their body weight and feed consumption were observed for one week. The results are shown in Table 9.

TABLE 8-(a)

| Basal ration II | |
|---|---|
| Ingredient | % |
| Sucrose | 55.7 |
| Soybean oil meal | 29.3 |
| Alfalfa meal | 2.0 |
| white fish meal | 8.0 |
| Animal fat | 3.2 |
| Calcium carbonate | 0.3 |
| Calcium phosphate | 0.7 |
| Salt | 0.2 |
| DL-methionine | 0.15 |
| Choline hydrochloride | 0.05 |
| Vitamin premix*[1] | 0.2 |
| Mineral premix*[2] | 0.2 |

Note:
*[1]Vitamin premix is composed of Vitamin A, $B_1$, $B_2$, $B_6$, $B_{12}$, $D_3$ and E, biotin, folic acid and calcium pantothenate.
*[2]Mineral premix is composed of ferrous sulfate, manganese sulfate, zinc sulfate, cupric sulfate, cobalt sulfate and potassium iodide.

TABLE 8-(b)

| Feed composition fed to animals | |
|---|---|
| Feed composition fed to Control group | The above Basal ration II |
| Feed composition fed to Treatment group I | The above Basal ration II + WS-1627 B 10 ppm |
| Feed composition fed to Treatment group II | The above Basal ration II + WS-1627 B 50 ppm |

TABLE 9

|  | Control group | Treatment group I | Treatment group II |
| --- | --- | --- | --- |
| Average initial body weight gain (g) | 88.5 | 88 | 88 |
| Average final body weight (g) at one week after the feeding | 183.8 | 204.5 | 209 |
| Average body weight gain (g) at one week after the feeding | 95.3 | 116.5 | 121 |
| Efficiency of feed utilization* | 2.02 | 2.00 | 1.67 |

*Note:

$$\text{Efficiency of feed utilization} = \frac{\text{Feed composition (g) utilized for one week}}{\text{Average body weight gain (g)}}$$

EXAMPLE 7

Injection Preparation

Some sterile samples of WS-1627B are distributed into vials, thereby containing 100 mg of the active ingredient. The vials are sealed hermetically to exclude bacteria. Whenever the vials are required for use, 2 ml of sterile distilled water for injection is added to the vial and the vial is subjected to administration.

TABLE 10

| Example 8 [Feed preparation] | |
| --- | --- |
| Ingredient | |
| Skim milk | 270 kg |
| Dried whey | 100 kg |
| fish meal | 50 kg |
| Wheat flour | 350 kg |
| Glucose | 50 kg |
| Tallow | 30 kg |
| Dried yeast | 100 kg |
| Starch | 21 kg |
| Casein sodium | 10 kg |
| Tricalcium phosphate | 10 kg |
| Sodium chloride | 4 kg |
| DL-Methionine | 500 g |
| Lysine hydrochloride | 1 kg |
| Vitamin A D E premix | 2 kg |
| Vitamin B premix*[1] | 2 kg |
| Trace mineral premix*[2] | 1 kg |
| WS-1627 B | 100 g |

Note:
*[1]Vitamin B premix is composed of vitamin $B_1$, vitamin $B_2$, vitamin $B_6$, vitamin $B_{12}$, biotin, folic acid and calcium pantothenate.
*[2]Trace mineral premix is composed of ferrous sulphate, manganese sulphate, zinc sulphate, cupric sulphate, cobalt sulphate and potassium iodide.

We claim:

1. A method for promoting growth of growing animals in need thereof which comprises administering to said animals a promotant effective amount of a compound selected from the group consisting (1) WS-1627A of the formula

$R_1 = COCH_3$
$R_2 = H$ (2) WS-1627B of the formula

$R_1 = COCH_3$
$R_2 = H$ (3) WS-1627C of the formula $R_1 = H$
$R_2 = COCH_3$ and (4) WS-1627D of the formula $R_1 = H$
$R_2 = COCH_3$ or their salts.

2. The method of claim 1 which comprises administering an admixture of said compounds WS-1627A, WS-1627B, WS-1627C and WS-1627D, or their salts.

3. The method of claim 1 which comprises administering the compound WS-1627C, or its salt.

* * * * *